United States Patent
Angelsen et al.

(10) Patent No.: US 11,796,659 B2
(45) Date of Patent: Oct. 24, 2023

(54) SUPPRESSION OF MULTIPLE SCATTERING NOISE IN PULSE ECHO IMAGING

(71) Applicant: SURF Technology AS, Trondheim (NO)

(72) Inventors: Bjørn A J Angelsen, Trondheim (NO); Stian Solberg, Florvåg (NO)

(73) Assignee: SURF TECHNOLOGY AS, Trondheim (NO)

( * ) Notice: Subject to any disclaimer, the term of this patent is extended or adjusted under 35 U.S.C. 154(b) by 410 days.

(21) Appl. No.: 16/911,170

(22) Filed: Jun. 24, 2020

(65) Prior Publication Data
US 2020/0405268 A1    Dec. 31, 2020

Related U.S. Application Data

(60) Provisional application No. 62/866,304, filed on Jun. 25, 2019.

(51) Int. Cl.
*G01S 7/52* (2006.01)
*G01S 15/87* (2006.01)
*G01S 15/89* (2006.01)

(52) U.S. Cl.
CPC ...... *G01S 7/52077* (2013.01); *G01S 7/52046* (2013.01); *G01S 15/878* (2013.01); *G01S 15/89* (2013.01); *G01S 15/8918* (2013.01)

(58) Field of Classification Search
CPC ............. G01S 7/52077; G01S 7/52046; G01S 15/878; G01S 15/89; G01S 15/8918
USPC .......................................................... 702/91
See application file for complete search history.

(56) References Cited

U.S. PATENT DOCUMENTS

| | | | |
|---|---|---|---|
| 9,291,493 B2 | 3/2016 | Angelsen | |
| 2012/0095699 A1 | 4/2012 | Angelsen et al. | |
| 2014/0150556 A1* | 6/2014 | Angelsen | G01N 29/343 73/596 |
| 2017/0343656 A1 | 11/2017 | Angelsen | |

FOREIGN PATENT DOCUMENTS

WO    WO 2019/145785    8/2019

OTHER PUBLICATIONS

Written Opinion and Search Report dated Sep. 23, 2020 issued in International Patent Application No. PCT/IB2020/000502.

* cited by examiner

*Primary Examiner* — Aditya S Bhat
(74) *Attorney, Agent, or Firm* — Cozen O'Connor

(57) ABSTRACT

Methods and instrumentation for pulse scattering estimation and imaging of scattering parameters in a material object by transmitting a pulse along a transmit beam and directing a receive beam that crosses at least one transmit beam at an angle <45 deg. The receive beam is at least in an azimuth direction at the transmit beam, and records scattered receive signal from the overlap region. A receive interval of the receive signal is gated for further processing to form measurement and/or image signals from cross-beam observation cells.

8 Claims, 5 Drawing Sheets

BACKGROUND

SUPPRESSION OF MULTIPLE SCATTERING NOISE IN PULSE ECHO IMAGING

RELATED APPLICATIONS

This application claims priority from U.S. Provisional Patent Application Ser. No. 62/866,304 which was filed on Jun. 25, 2019, the entire content of which is incorporated herein by reference.

BACKGROUND OF THE INVENTION

1. Field of the Invention

The present invention is directed to methods and instrumentation for imaging of objects. Imaging with acoustic pressure waves is shown as an example, but the methods are also useful for imaging with shear elastic waves and coherent electromagnetic waves. Applications of the invention are for example, but not limited to, medical imaging and therapy, non-destructive testing, industrial and biological inspections, geological applications, SONAR and RADAR applications.

2. Description of the Related Art

Pulse echo measurements are used to form images with ultrasound, SONAR, RADAR, and Laser. Multiple scattering of the transmitted pulse then often adds disturbing noise to the images. The methods and instrumentation principles are applicable to all of ultrasound, SONAR, RADAR, and Laser, but for simplicity ultrasound imaging is used to describe essentials of methods and instruments.

As a background, FIG. 1 is a typical example of how multiple scattering noise is generated in the process of ultrasound pulse echo imaging, and how it reduces the quality of the back-scatter ultrasound images. 101 shows by example a linear array ultrasound probe at the body surface 100 with a blood vessel 102 where the target is to image an atheroma 103 of the posterior vessel wall 104. To generate a 2D ultrasound image with current systems, ultrasound pulses are transmitted along a set of transmit beams that are laterally scanned across the object. The back scattered ultrasound pulses from the object are picked up by the array probe along receive beams with the same axis as the transmit beam. The received back-scattered signal from at least one pulse per transmit beam is processed to form an image signal with depth along the combined axis of the transmit and receive beams. By scanning the transmit and receive beams within a 2D or 3D region of the object, a 2D or 3D image of the object is formed.

Multiple scattering noise is formed by strong scatterers in front of the interesting part of the object, for example a fat layer 105 close to the transducer in front of the vessel. This fat layer produces a strong reflection of the transmitted pulse that propagates back to the transducer array where it is reflected a $2^{nd}$ time from the transducer surface 106 and re-emitted towards the vessel where it is reflected a $3^{rd}$ time at the front vessel wall 107 and propagates back to the transducer array following the path 108, and received together with the $1^{st}$ order scattered pulses from the atheroma 103 that follows the path 109.

Typical $1^{st}$ order scattered pulses are shown along the depth/time axis 110, where the upper pulse 110a is the $1^{st}$ order reflection from the fat layer, 110b is the $1^{st}$ order reflection from the anterior vessel wall, and 110c is reflections from the atheroma 103. The propagation time lag for the $3^{rd}$ order scattered pulse following the path 108 is similar to the $1^{st}$ order reflected pulses from the atheroma 103 and appears as a $3^{rd}$ order multiple scattering noise shown as 111a along the depth/time axis 111. This $3^{rd}$ order multiple scattering adds to the $1^{st}$ order scattered signal 110c as noise that hampers the diagnostic process.

The pulse amplitude decreases in each scattering, so that more than $3^{rd}$ order scattering rarely produces important noise in the images. Thus, the analysis and description of $3^{rd}$ order scattering as the situation for higher order scattering can easily be deduced from this description. In the above example, the $2^{nd}$ scatterer is the transducer array, while we note that other strong scatterers between the $1^{st}$ scatterer and the transducer can also produce problematic $3^{rd}$ order scattering noise. Also, a reverse path of 108 where the transmitted pulse is scattered a $1^{st}$ time from the front vessel wall 107 and the scattered pulse propagates back to the transducer surface 106 for a $2^{nd}$ scattering into the tissue followed by a $3^{rd}$ scattering from the fat layer 105, produces a $3^{rd}$ order multiple scattered pulse with the same delay as 111a. We call the path where the scatterer closest to the transducer is the $1^{st}$ scatterer for Class I scattering, while the path where the scatterer furthest from the transducer is the $1^{st}$ scatterer for Class II scattering. In some cases the $1^{st}$ and the $3^{rd}$ scatterer can be the same scatterer where Class I and II produces the same $3^{rd}$ order scattered pulse.

Nonlinear self-distortion of the forward propagating transmit pulse introduces harmonic components of the fundamental band of the transmit pulse that in the near field increases relative to the fundamental amplitude with depth. At the $1^{st}$ scattering, the pulse amplitude drops so much that we can neglect harmonic distortion of the forward propagation of the scattered pulse. When the $1^{st}$ scatterer (e.g. 105) is much closer to the transducer than the object scatterer (e.g. 103), the harmonic component of the received $3^{rd}$ order scattered pulse 111a is relatively much lower than for the $1^{st}$ order scattered pulse 110c from the atheroma. With the well-known harmonic imaging method one selects the harmonic band for imaging through filtering or pulse inversion. This method hence suppresses multiple scattering noise where the $1^{st}$ scatterer is close to the transducer, i.e. Class I noise, in the image. However, for Class II noise where the $1^{st}$ scatterer is at a depth, like 107, harmonic imaging does not provide good relative suppression of the noise.

To help this situation, disclosed are methods and instrumentation for strong suppression of both Class I and Class II noise. The method can operate on the fundamental band of the transmitted pulse that provides better penetration depth with a given frequency, or for a defined depth allows the use of higher frequencies than the harmonic imaging method. The method can also be combined with harmonic imaging to provide improved suppression of multiple scattering noise.

SUMMARY OF THE INVENTION

This summary gives a brief overview of components of the invention and does not present any limitations as to the extent of the invention, where the invention is solely defined by the claims appended hereto.

The current invention provides methods and instrumentation for estimation and imaging of propagation and scattering parameters in a material object. The methods have general application for both acoustic and shear elastic waves such as found in SONAR, seismography, medical ultrasound imaging, and ultrasound nondestructive testing, and also coherent electromagnetic waves such as found in RADAR and laser imaging. In the description below one uses acoustic waves as an example, but it is clear to anyone skilled in the art how to apply the methods to elastic shear waves and coherent electromagnetic waves.

In its broadest form the methods comprises transmitting at least one pulse along at least one transmit beam and directing at least one receive cross-beam that crosses each said at least one transmit beam at an angle, typically less than 60 deg. Said receive cross-beam is at least in an azimuth direction focused at said transmit beam, and records scattered receive signal from the overlap region between said at least one transmit and said at least one receive cross-beam. A receive interval of the receive signal is gated out to form a cross-beam receive signal for further processing to form measurement and/or image signals from cross-beam observation cells. In a preferred embodiment the axis of said at least one transmit and receive cross-beams crosses each other with the receive beam focus at the transmit beam axis, and the receive interval is centered at the transmit beam axis with a typical duration less than 10 oscillation periods of the receive signal.

The invention is also directed to devices to transmit pulses along beams that are wide in at least one direction where the pulse wave fronts are approximately plane in at least said direction. Transmitting such plane waves in several directions one can combine the received signals from the different directions to form synthetic transmit beams focused at different locations within a 2D or a 3D region, according to known methods. The receive signal from the different receive elements are processed to form synthetic receive cross-beams to the synthetic transmit beams to form measurement and/or image signals from cross-beam observation cells along each synthetic transmit beam.

With a single azimuth direction azimuth plane wave, one can obtain spatial resolution with regular back-scatter registration of several parallel, dynamically focused receive beams, where time of arrival of scattered pulses produces spatial resolution along the depth of each receive cross-beam, while the receive cross-beam focusing and time gating of the received signal produces lateral spatial resolution, all according to known methods, for example, as described in U.S. Pat. No. 9,921,493. This method is however more sensitive to multiple scattering noise than the receive cross-beam method with physically or synthetically focused transmit beams.

A main advantage with the receive cross-beam method is that multiple scattering signals are time-gated out by the crossing receive beams and the selection of the cross-beam receive signal interval. Typical image signals obtained by further processing of the gated cross-beam receive signals are estimates of of i) a function of the average or the peak of a the amplitude or power of the cross-beam receive signal, and ii) a function of the amplitude of the cross-beam receive signal at a sample close to the axis of the transmit beam, and of iii) the local displacement of the object, and ii) one or more components of the local displacement of the object, and iv)) the local strain of the object, and v) one or more components of the local strain of the object.

2D and 3D images are formed by scanning the transmit beam with matched crossing receive beams across a 2D or 3D region of the object, and processing the receive signals for the cross-beam observation cells in the 2D or 3D region.

In general said at least one HF receive cross-beam is focused on the HF transmit beam axis forming a cross-beam observation cell as the cross-over region of the HF transmit and HF receive cross-beams. The invention devices spatial filtering of the gated receive signals from multiple cross-beam observation cells to produce synthetic focusing of the observation cells.

The invention also describes instruments for carrying through the measurements and processing according to the invention. With one version of the instrument, cross beam receive signals are generated in dedicated beam forming HW according to known methods, and digital HF receive signals are transferred to the processing structure for storage and further processing in a general SW programmable processor structure of different, known types.

In another version of the instrument the individual receiver element signals are digitized and transferred to the memory of a general SW programmable processor structure where the receive beam forming and further processing is SW programmed.

The instrument comprises a display system for display of estimated parameters and images according to known technology, and user input to the instrument according to known methods.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

DETAILED DESCRIPTION OF THE EMBODIMENTS

Example embodiments of the invention will now be described in relation to the drawings. The methods and structure of the instrumentation are applicable to both electromagnetic (EM) and elastic (EL) waves, and to a wide range of frequencies with a wide range of applications. For EL waves one can apply the methods and instrumentation to both shear waves and compression waves, both in the subsonic, sonic, and ultrasonic frequency ranges. We do in the embodiments describe by example ultrasonic measurements or imaging, both for technical and medical applications. This presentation is meant for illustration purposes only, and by no means represents limitations of the invention, which in its broadest aspect is defined by the claims appended hereto.

Figure 1:
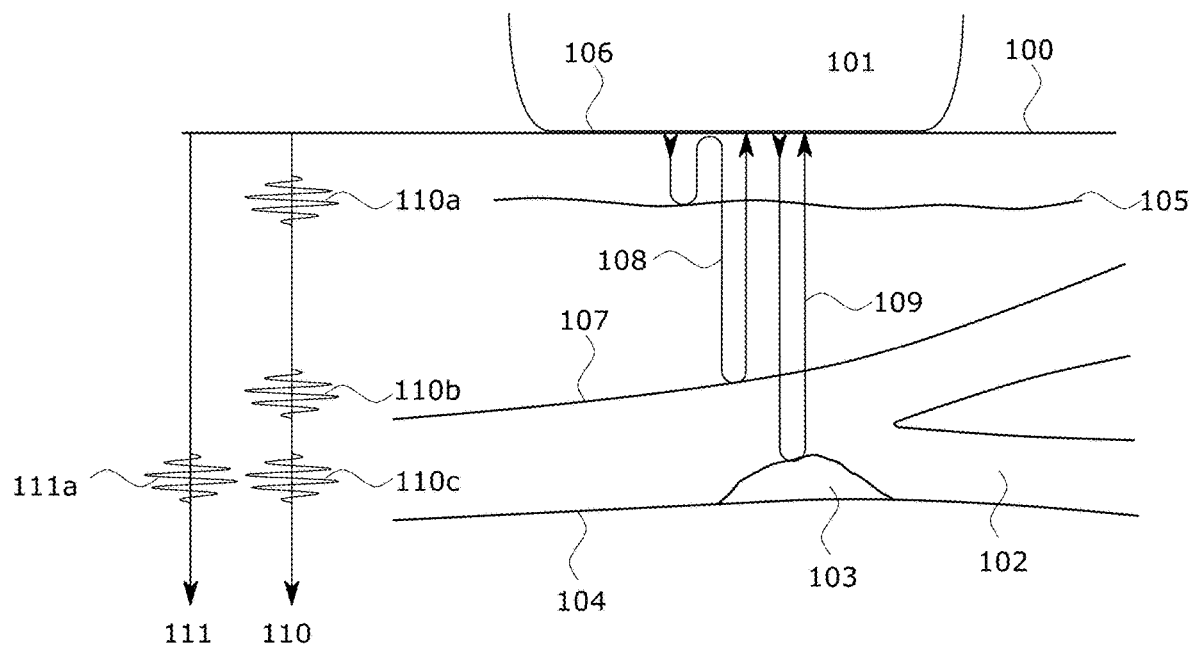
FIG. 1 shows how multiple scattering adds noise to a typical Prior Art scanning system
Figure 2:
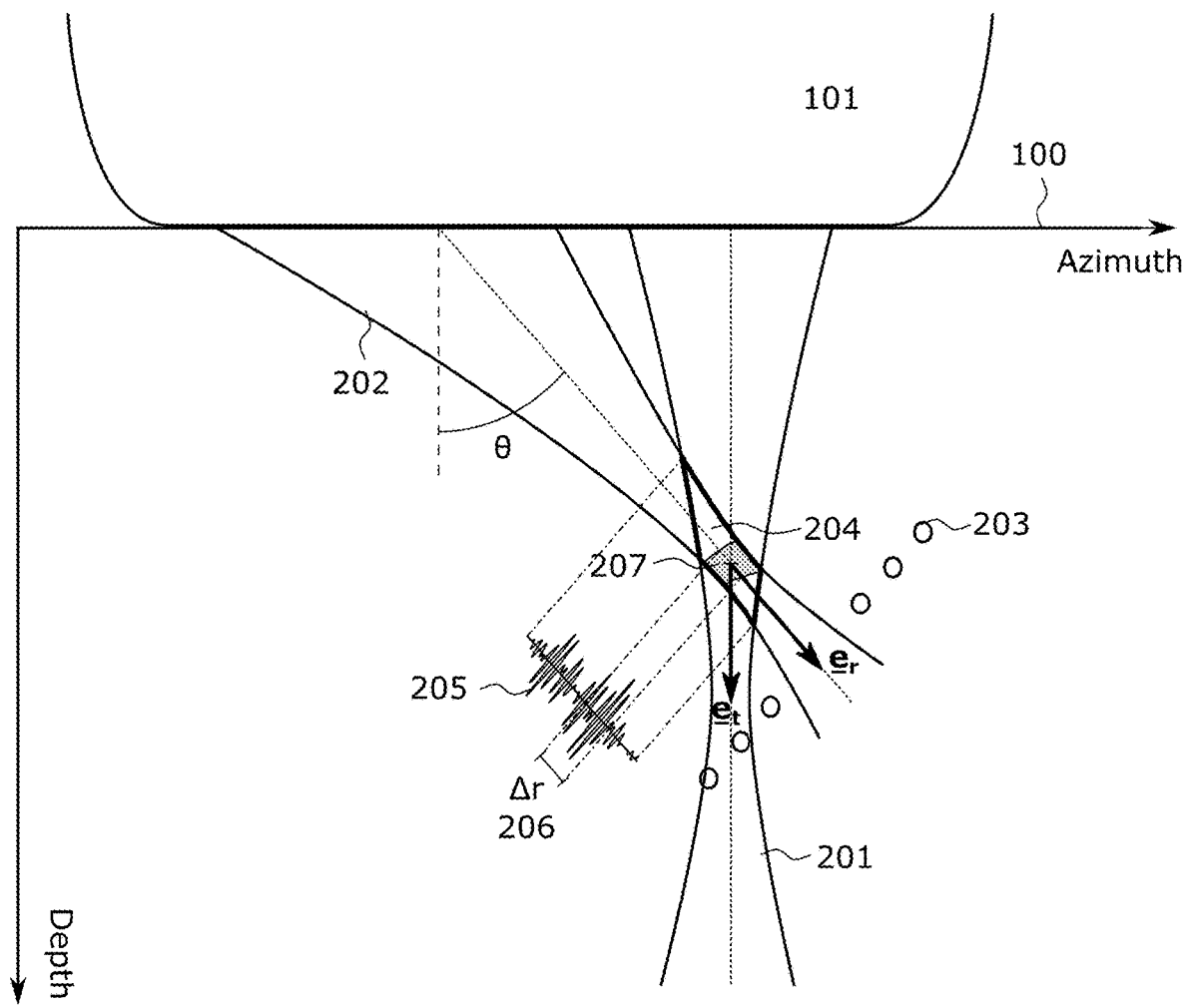
FIG. 2 shows an example crossing transmit and receive beam arrangement that suppresses the effect of multiple scattering noise according to the invention

Embodiments of the invention present method to suppress the multiple scattering noise in the image by using a set of receive beams that crosses the transmit beam, where an example is illustrated in FIG. 2. The Figure shows the same ultrasound probe 101 on the body surface 100 as in FIG. 1, with one example transmit beam 201.

The receive signal from all array elements are transferred to a processor that performs multiple combinations of the element receive signals to form a set of parallel receive beams that crosses the transmit beam at different depths. One example receive cross-beam is shown as 202, where the dots 203 indicates further parallel receive beams crossing the transmit beam 201 at different depths. For 2D or 3D imaging of a region of the object, the transmit beam is scanned across said 2D or 3D region, and the scattered signal from each transmit beam is observed with a matched set of receive cross-beams beams similar to 202/203.

The receive cross-beams are typically focused at least in an azimuth direction at said transmit beam at different depths, forming cross over regions between the transmit beams and the matched cross-over receive beams, where 204 shows the cross-over region for the shown transmit and receive beams 201 and 202. 205 shows an example receive signal scattered from the cross-over region 204. A cross-beam receive signal 206 is for further processing gated out from 205 along a depth interval $T$ and represents the signal scattered from object structures in the cross-beam observation cell 207, which due to the signal range gating is smaller than the cross-over region 204. In a preferred embodiment the axis of receive cross-beams crosses the axis of the matched transmit beam with the azimuth receive beam focus at the matched transmit beam axis, and the receive interval is centered at the transmit beam axis with a typical duration less than ~10 oscillation periods of the receive signal. With this crossing arrangement between the transmit and matched receive cross-beams, the gated cross-beam receive signal 206 has very low content of multiple scattering noise. Spatial filtering of the signals from neighboring cross-beam observation cells as in Eqs. (1, 2) can be done to produce a synthetic cross-beam observation cell with reduced dimension. Such filtering can also through interpolation introduce intermediate image points that produces smoothness in the images. The signal 206 directly, or the filtered signals according to Eqs. (1, 2), are first image signals with strong suppression of multiple scattering noise, and are further processed to produce image further image signals, with specific object information with highly suppressed influence of multiple scattering noise.

Image signals that represent the scattering strength of object structures within the cross-beam observation cells, can for example be obtained as a function of the average or maximal value of the amplitude or power of the cross-beam receive signal 206, or even a single sample of 206 close to the transmit beam axis. Another interesting image signal represent estimates of local displacement $\underline{\psi}(\underline{r},t)$ of the object, where $\underline{r}$ is the spatial position of the center of the cross-beam observation cell, t is so-called slow time representing object movements, and $\underline{\psi}$ is an average of the object displacement around $\underline{r}$. Estimates of $\underline{\psi}(\underline{r},t)$ can be obtained through spatial correlation between scattering signals from two consecutive 2D or 3D images according to known methods. The advantage according to invention, is the low level of multiple scattering noise in the cross-beam receive signal as a basis for estimating $\underline{\psi}(\underline{r},t)$. With the well-known method of elastography one can obtain object strain from estimates of the spatial gradient of $\underline{\psi}(\underline{r},t)$, that gives a depiction of spatial variation in object elastic stiffness.

Estimates of the components of the local displacement of the object within the cross-beam observation cell 207 can also be estimated from the average phase difference between cross-beam receive signal 206 from two transmitted pulses. For an average local vector displacement $\underline{\psi}(\underline{r},t)$ of the object within the cross-beam observation cell centered at the position $\underline{r}$, the average phase difference between the cross-beam receive signal 206 from two consecutive transmit pulses at slow time t is $$\theta(\underline{r},t) = -2\pi(\underline{e}_t + \underline{e}_r) \underline{\psi}(\underline{r},t)/\lambda \qquad (1)$$

where $\underline{e}_t$ and $\underline{e}_r$ are the unit vectors along the transmit beam and receive cross-beam through the observation cell, and $\lambda$ is the center wave length of the transmitted pulse. This means that we can obtain estimates of the component of the displacement vector along the vector $\underline{e}_t + \underline{e}_r$ from estimates of this average phase difference. With two receive cross-beams crossing the transmit beam at the same location, for example as 404 and 405 in FIG. 4, one obtains estimates of two components of the displacement vector along $\underline{e}_t + \underline{e}_{r1}$ and $\underline{e}_t + \underline{e}_{r2}$ within the 2D plane. To obtain estimates of a $3^{rd}$ component of $\underline{\psi}(\underline{r},t)$ in 3D space with this method, one must also direct a receive cross-beam that crosses through the 2D plane. One can also use more than two consecutive pulses to obtain lower estimation variance for the average phase difference. This method has similarities to Doppler measurements of local object velocities, but due to the low level of multiple scattering noise in the cross-beam receive signal 206, this phase based method do not require clutter filtering common in Doppler measurements, and hence allows estimates of lower displacements than with the Doppler method.

Figure 3:
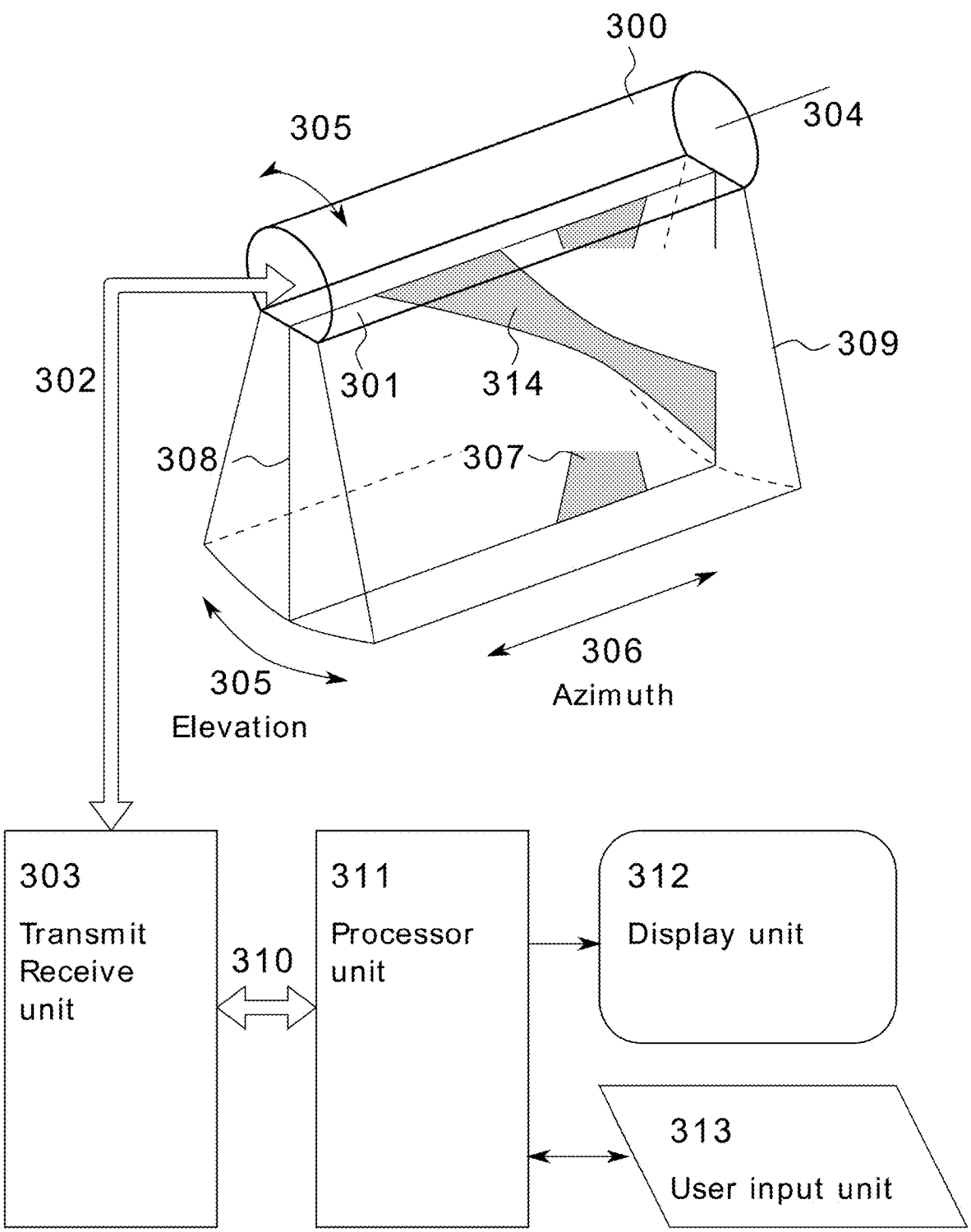
FIG. 3 shows a block diagram for an example instrument according to the invention.

FIG. 3 shows a block diagram of an example instrument for carrying out imaging according to this method. 300 shows a 3D ultrasound probe comprising a linear array 301 with a set of N elements in an azimuth direction indicated by the arrows 306. The linear array can be made according to known methods. The array elements are via a cable 302 connected to a transmit/receive unit 303 that connects each element to transmit/receive circuits comprising a transmit amplifier and a receive amplifier where the output of the receive amplifier is further connected to an analog to digital converter (A/D) presenting a digital representation of the received signals from all receive elements, according to known methods. The AD converter can in a modified embodiment present digital representations of the I-Q components of the receive signals from each element that represents the same information as the radio frequency (RF) signal, according to known methods.

For 3D scanning of the ultrasound beams, the linear array 301 can in this example embodiment be rotated around the long axis 304 that provides a mechanical scanning of the transmit/receive beams in an elevation direction, indicated by the arrows 305. For each elevation position of the array, one does electronic scanning of the transmit beam in an azimuth direction indicated by the arrows 306, through electronic selection of transmitting elements, and transmitting pulse complexes similar to what is shown in FIG. 1/2, with selected beam directions and focus. An example transmit beam is illustrated schematically as 307 within a 2D azimuth plane 308 with given elevation position within a total 3D scan volume 309. Alternative elevation movements of the array, like side-ways movement can equivalently be done according to known methods, depending on the space available for such movement, and the shape of the object.

Two versions of the instrument are useful, where in the first version 303 comprises beam former for a set of receive cross-beams, where one receive cross beam is illustrated as 314 in the 2D scan plane 308, and back scatter receive beams with the same axis as the transmit beam 307. In a preferred embodiment the back-scatter receive beam is equal to the transmit beam as this improves suppression of multiple scattering noise in the back-scatter receive signal, as discussed in U.S. Pat. No. 9,291,493. During the scan, the cross-beam and back-scatter receive signals are via the high speed bus 310 transferred to the processor 311 for storage and further processing.

The processor 311 comprises a multicore central processing unit (CPU) and typically also a graphics processor unit (GPU) that are SW programmable. The processor receives user inputs from a user/operator input unit 313 that operates according to known methods, and displays image data and other information necessary for communication with the user/operator through a combined display and audio unit 312, according to known methods.

In the second version, the digital HF receive signals from each HF receive element and each transmitted pulse complex are via the high speed bus 310 transferred to the processor 311 for storage and further processing. In this second version, a SW program in the processor 311 combines receive signals from multiple receive elements and produces a set of receive cross-beams crossing each HF transmit beam in the 2D set, for example as described in relation to FIG. 2. In this example a SW program also produces a set of back-scatter receive signals from back-scatter receive beams with the same axis as the HF transmit beams, and preferably also equal to the HF transmit beams.

Let $Y(\omega, \underline{r}_0)$ be the temporal Fourier transform the received signal from a cross-beam observation cell centered around $\underline{r}_0$. When 3D scanning of a stationary object is available, one can obtain synthetically focused transmit and receive beams through spatial filtering of measurement signals as $$\hat{Y}(\omega,\underline{r})=\int d^3r_0 W(\omega,\underline{r}-\underline{r}_0,\underline{r})Y(\omega,\underline{r}_0)$$

$$W(\omega,\underline{r}-\underline{r}_0,\underline{r})=B(\omega,\underline{r}-\underline{r}_0,\underline{r})e^{i\omega\tau_f(\underline{r}-\underline{r}_0,\underline{r})}$$

$$\tau_f(\underline{r}-\underline{r}_0,\underline{r})=\tau_t(\underline{r}-\underline{r}_0,\underline{r})+\tau_r(\underline{r}-\underline{r}_0,\underline{r}) \quad (1)$$

where $\tau_t$ and $\tau_r$ are delays produced by the shape of the transmit and receive beam wave fronts, and B is a weighting function to reduce spatial side-lobes of the filter. The filter kernel can be obtained from simulation of the transmit and receive beams to obtain $\tau_t(\underline{r}-\underline{r}_0,\underline{r})$ and $\tau_r(\underline{r}-\underline{r}_0,\underline{r})$. The filter amplitude weighting B, can conveniently be proportional to the amplitude of the simulated beams, potentially with added windowing. This filtering reduces the dimension of the cross-beam observation cells and can also produce intermediate image points that increases the image smoothness through interpolation.

When the receive beam is focused onto the transmit beam axis, we can approximate $\tau_r \approx 0$ within in the observation region. The integration is then done over the transversal coordinate to the transmit beam axis, $\underline{r}_\perp=(x,y)$, as $$\hat{Y}(\omega,\underline{r})=\int d^2r_\perp W(\omega,\underline{r}-\underline{r}_\perp,\underline{r})Y(\omega,\underline{r}_\perp)$$

$$W(\omega,\underline{r}-\underline{r}_\perp,\underline{r})=B(\omega,\underline{r}-\underline{r}_\perp,\underline{r})e^{i\omega\tau_t(\underline{r}-\underline{r}_\perp,\underline{r})} \quad (2)$$

When the y-width of the receive beam focus is sufficiently narrow, the integration over $\underline{r}_\perp$ can be approximated by an integration in the x-direction (azimuth) only, with a filter adapted for use with 2D scanning of the transmit beam in the x-direction.

The invention also devices to transmit pulses along beams that are wide in at least one direction where the pulse wave fronts are approximately plane in at least said direction. Transmitting such plane waves in several directions one can combine the received array element signals from several pulses and transmit beam directions to form a set of synthetic cross-beam receive signals from a set of synthetic cross-beam observation cells produced by the cross-over regions between a set of synthetic transmit beams and a matched set of synthetic receive cross-beams, according to known methods as described in U.S. Pat. No. 9,291,493. The synthetic received signals from said synthetic receive cross-beams are used in the further processing to form image signals of object structures.

With a single direction plane pulse wave, one can obtain spatial resolution with regular back-scatter registration of several parallel, dynamically focused receive beams, where time of arrival of scattered pulses produces spatial resolution along the depth of each receive cross-beam, while the receive beam focusing and time gating of the received signal produces lateral spatial resolution, all according to known methods. This method is however more sensitive to multiple scattering noise than the cross-beam method with physically or synthetically focused transmit beams.

Through well known methods of radiofrequency filtering of the receive signal, or the use of pulse inversion where one transmits two pulses with opposite polarity of the pulse, one can extract harmonic components of $Y(\omega,\underline{r})$ for further processing in the receive processor, as described in FIG. 3. Use of the harmonic component of the transmit band for receive processing provides a further add-on to the suppression of multiple scattering noise, according to known methods.

Figure 4A:
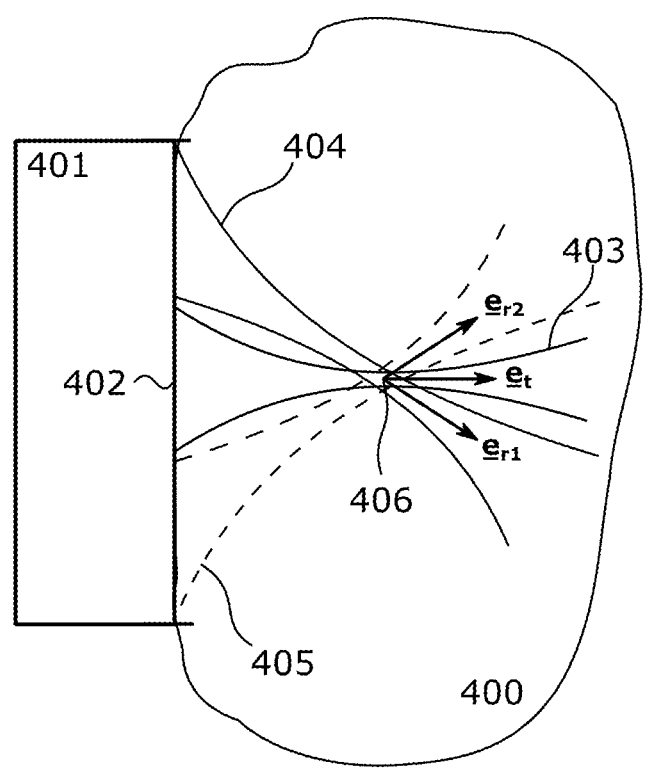
FIG. 4a shows an example of more than one receive beam crossing the transmit beam at the same depth to provide more than one receive signal that allows reduction in speckle noise for the estimated image signals.

To reduce variance of the image signal estimates, one can use more than one receive cross beam that crosses the transmit beams at the same location, where an example is shown in FIG. 4a using the same type of linear array probe 401/101 on the surface 402/100 of the object 400, as shown in FIGS. 1 and 2. In a first example 403 shows a transmit beam. Receive elements are selected from the array elements to define receive cross-beams where 404 and 405 shows two example cross-beams that crosses the transmit beam at the same location 406 at different angles. The receive signals for both receive beams are gated around the axis of the transmit beam at the same depth to pick up scattered signals from by en large the same scatterers around the transmit beam axis. However, due to the different directions for the two receive beams the relative arrival time from the different scatterers will be different for the signals from the two beams, and hence the speckle of the signals will be different. Averaging the processed image signals from the receive beams will hence provide image signals with less speckle noise. It is clear that one can also use more than two receive beams with different directions to further improve the estimated image signals.

The strong angular steering of the receive beams in FIGS. 2 and 4a requires down to $0.5*\lambda$ pitch of the array, where $\lambda$ is the wavelength in tissue. For current linear arrays a typical pitch ~$1.5*\lambda$, and the low pitch hence increases the required number of elements to get the same width of the image. A larger pitch can be allowed by using an angled transmit beam, for example as 404, at a low frequency, say at the lower end of the effective frequency band of the array with a tissue wave length $\lambda_t$, and utilizing for receive processing a harmonic component of the received signal at the upper end of the effective frequency band of the array with direct forward receive cross-beams, for example as 403. The direct forward receive beams set weaker requirements on the pitch of the array, for example up to ~1.5 times the harmonic wavelength $\lambda_r = \lambda_t/2$ in the tissue. This gives a receive requirement of an array pitch of $0.75*\lambda_t$, which allows a directional steering of the transmit beam up to ~50 deg from the array normal.

Figure 4B:
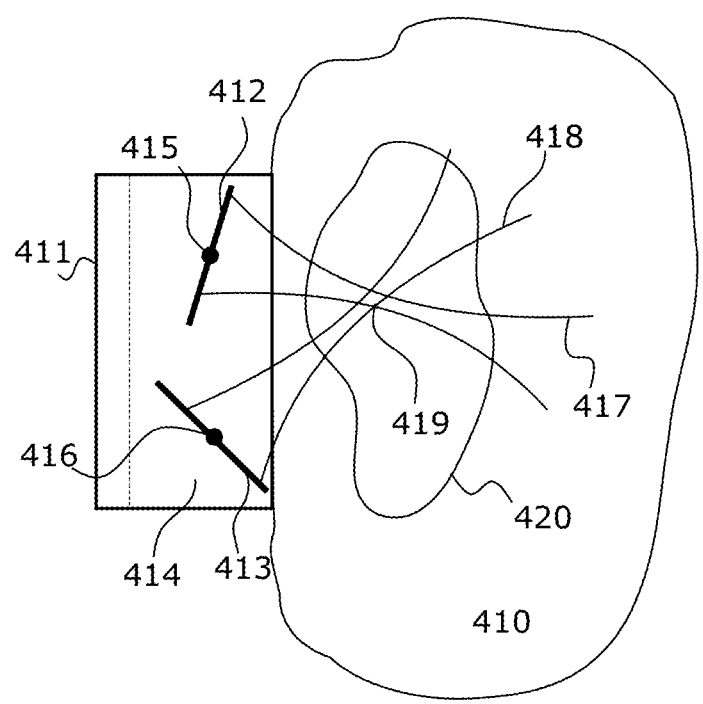
FIG. 4b shows an example of angled arrays that allows the use of larger array pitch and also annular arrays with mechanical direction steering of the beams.

FIG. 4b shows a modification that allows the use of larger pitch of the elements, and also the use of annular arrays and even fixed focus transducers, to estimate linear and nonlinear wave propagation and scattering parameters in a cross-beam observation cell 419 of the object 410. 411 shows a combined transmit and receive system that comprises a transmit array 412 and a receive array 413, embedded in a fluid filled region 414 to provide wave propagation contact to the object. Embedded in the fluid also allows mechanical rotation of the arrays around the axes 415 and 416, or other mechanical movement of the arrays, potentially in combination with electronic scanning of the beam directions according to known methods. The transmit array is connected to a transmit beam former inside the system 411 where an example resulting transmit beam is shown schematically as 417. The receive array 413 is connected to a receive beam former inside 411 that is used to define HF receive beams, for example schematically as one example receive beam 418, and further connected to a receive processing system according to the methods described in relation to FIGS. 2 and 3. The beam formers and processing structures operates and are implemented according to known methods, and details are therefore not shown in the Figure. The system allows crossing HF transmit and receive beams with an overlap 419 that defines the transmit-receive cross-beam observation cell 419 that by example can be scanned within a region of the object, exemplified with 420, by scanning one or multiple receive and/or transmit beams as described in relation to FIG. 2.

The coupling medium 414 between the transmit and receive arrays (412, 413) and the object allows the transmit and receive arrays to have an angle to the object surface, which hence allows for larger pitch of the array elements. With linear arrays one can scan the transmit and receive beams side-ways for imaging of linear and nonlinear propagation and scattering parameters as presented in relation to FIG. 2. Mounting the transmit and receive arrays 412 and 413 to rotating shafts 415 and 416, respectively, allows mechanical scanning of the transmit and receive beams that enlarges the number of measurement observation regions that can be obtained. The arrays 412 and 413 can then be reduced to annular arrays with sharp symmetric focusing, and even fixed focused transducers for a limited number of cross beam observation regions. Mechanical scanning of the beams in an elevation direction (normal to the paper plane) also opens for 3D imaging of regions of the object with methods according to this invention, as described in FIG. 3. These solutions also allow for low cost systems for estimation of linear and nonlinear propagation and scattering parameters in selected regions of an object.

It is expressly intended that all combinations of those elements and/or method steps, which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. An instrument for estimation of image signals from an object, comprising;
    means for transmitting at least one pulse along each of a set of transmit beams in different locations in the object;
    receive means for directing a set of receive cross-beams, matched to each transmit beam, that crosses the axis of the matched transmit beams at an angle >15 deg at different depths along each transmit beam, to form matched cross-over regions between said receive cross-beams and said matched transmit beams at said different depths along said transmit beams;
    means for recording signals scattered from object structures within said matched cross-over regions;
    means for gating out an interval of each said recorded signals to form cross-beam receive signals scattered from cross-beam observation cells at different depths along each transmit beams, and
    means for processing said cross-beam receive signals to provide image signals for each cross-beam observation cell.

2. The instrument according to claim 1, wherein
    said means for transmitting transmit beams that are wide at least in one direction and the pulse phase fronts are close to plane in said direction;
    said receive means comprises means for combining the receive signals from the array elements from several pulses and transmit beam directions, to form a set of synthetic cross-beam receive signals from a set of synthetic cross-beam observation cells produced by the cross-over between a set of synthetic transmit beams and a matched set of synthetic receive cross-beams; and
    said means for processing comprises means for processing of the set of synthetic cross-beam receive signals to obtain image signals.

3. The instrument according to claim 1, where said means for processing comprises means to provide image signals proportional to an estimate of one of i) a function of the average or the peak of a the amplitude or power of the cross-beam receive signal, and ii) a function of the amplitude of the cross-beam receive signal at a sample close to the axis of the transmit beam.

4. The instrument according to claim 1, where said means for processing comprises means to provide image signals proportional to an estimate of one of i) the local displacement of the object, and ii) one or more components of the local displacement of the object, and iii)) the local strain of the object, and iv) one or more components of the local strain of the object.

5. The instrument according to claim 1, where said receive means comprises means to provide more than one receive cross-beam that crosses each transmit beam at the same depth, and said means for processing combines the cross-beam receive signals from the more than one receive cross-beams to provide image signals for each cross-beam observation cell.

6. The instrument according to claim 1, comprising
    means for scanning both the transmit beam and the matched set of parallel receive cross-beams across a 2D or 3D region of the object, and
    said means for processing comprises means for using the processed image signals from the cross-beam observation cells at different depths along each transmit beam to form image signals representing 2D or 3D images of object parameters.

7. The instrument according to claim 1, where
said means for transmitting transmits ultrasound pulses at a low transmit frequency band with transmits beams at an angle >15 deg to the transmit array radiation surface, and
said receive means directs said receive cross-beams to said receive array radiation surface, and
said means for recording records a harmonic band of said low transmit frequency band,
to allow for a large pitch of the transmit and receive arrays with a highest frequency of the cross-beam receive signals.

8. The instrument according to claim 7, comprising means for filter combinations of a group of cross-beam receive signals from a group of cross-over regions to reduce the spatial resolution of cross-over regions.

* * * * *